US009265593B2

(12) United States Patent
Stewart et al.

(10) Patent No.: US 9,265,593 B2
(45) Date of Patent: Feb. 23, 2016

(54) FLOSSING SYSTEM

(75) Inventors: Jeromi Stewart, Santa Monica, CA (US); Keith Bornstein Allen, Santa Monica, CA (US)

(73) Assignee: OralWise, INC, Dallas, TX (US)

( * ) Notice: Subject to any disclaimer, the term of this patent is extended or adjusted under 35 U.S.C. 154(b) by 66 days.

(21) Appl. No.: 13/236,290

(22) Filed: Sep. 19, 2011

(65) Prior Publication Data
US 2012/0067367 A1 Mar. 22, 2012

Related U.S. Application Data

(60) Provisional application No. 61/384,799, filed on Sep. 21, 2010.

(51) Int. Cl.
*A61C 15/04* (2006.01)
(52) U.S. Cl.
CPC ............. *A61C 15/046* (2013.01); *A61C 15/048* (2013.01)
(58) Field of Classification Search
CPC .... A61C 15/02; A61C 15/043; A61C 15/046; A61C 15/048; A61C 9/0033
USPC ........................... 132/321, 323–324, 327–329
See application file for complete search history.

(56) References Cited

U.S. PATENT DOCUMENTS

| 882,204 | A | * | 3/1908 | Lassen | 223/99 |
|---|---|---|---|---|---|
| 3,799,177 | A | | 3/1974 | Bragg | |
| 3,835,872 | A | * | 9/1974 | Daniel | 132/324 |
| 4,304,246 | A | | 12/1981 | Yafai | |
| 4,519,408 | A | | 5/1985 | Charatan | |
| 4,655,233 | A | | 4/1987 | Laughlin | |
| 4,941,488 | A | | 7/1990 | Marxer et al. | |
| 4,966,176 | A | | 10/1990 | Lachenberg | |
| 4,982,752 | A | | 1/1991 | Rodriguez | |
| 5,010,906 | A | * | 4/1991 | Preciutti | 132/323 |
| 5,016,660 | A | | 5/1991 | Boggs | |
| 5,065,861 | A | | 11/1991 | Greene et al. | |
| 5,067,503 | A | * | 11/1991 | Stile | 132/324 |
| 5,123,432 | A | | 6/1992 | Wyss | |
| 5,127,415 | A | | 7/1992 | Preciutti | |

(Continued)

FOREIGN PATENT DOCUMENTS

| CA | 2356225 A1 * | 2/2003 |
|---|---|---|
| CN | 201500200 U | 6/2010 |
| FR | WO03063643 A1 | 8/2003 |

*Primary Examiner* — Rachel Steitz
*Assistant Examiner* — Jennifer Gill
(74) *Attorney, Agent, or Firm* — JP Webb; Jason P. Webb; Danny Y. H Cheng

(57) ABSTRACT

A flossing system including a cradle and a housing. The flossing system includes an array of floss cartridges having a length of floss. The array of floss cartridges include a pair of coupling members each coupled to opposite ends of the length of floss. Each floss cartridge includes a coupling structure. The flossing system includes a pair of floss handles disposed on the cradle and selectably coupleable to the coupling members. The pair of floss handles include a cylindrical body. The pair of floss handles include a release mechanism configured to selectably disengage the floss handle from the coupling member. The release mechanism includes an actuation member disposed through a back end of the cylindrical body of each of the pair of floss handles. The pair of floss handles each include a top aperture configured to receive the coupling structure of the pair of coupling members.

4 Claims, 5 Drawing Sheets

(56) References Cited

U.S. PATENT DOCUMENTS

| | | | | |
|---|---|---|---|---|
| 5,160,077 | A | 11/1992 | Sticklin | |
| 5,174,314 | A | 12/1992 | Charatan | |
| 5,190,200 | A | 3/1993 | Hammerlund | |
| 5,199,452 | A | 4/1993 | Cheng | |
| 5,222,510 | A | 6/1993 | Zuehlsdorf | |
| 5,224,501 | A | 7/1993 | McKenzie | |
| 5,299,723 | A | 4/1994 | Hempel | |
| 5,435,330 | A | 7/1995 | Dix | |
| 5,469,874 | A | 11/1995 | Meyer et al. | |
| 5,469,996 | A * | 11/1995 | Hurlimann | 223/99 |
| 5,477,871 | A | 12/1995 | Sanchez, Jr. | |
| 5,564,446 | A * | 10/1996 | Wiltshire | 132/323 |
| 5,570,710 | A | 11/1996 | Wei et al. | |
| 5,662,130 | A * | 9/1997 | Wiltshire | 132/323 |
| 5,685,325 | A * | 11/1997 | Wei et al. | 132/323 |
| 5,692,532 | A | 12/1997 | Gabrovsek | |
| 5,738,124 | A | 4/1998 | Cervato | |
| 5,775,346 | A | 7/1998 | Szyszkowski | |
| 5,778,906 | A | 7/1998 | Wei et al. | |
| 5,860,435 | A | 1/1999 | Hippensteel | |
| 5,881,744 | A | 3/1999 | Lo | |
| 5,915,392 | A | 6/1999 | Isaac | |
| 6,019,109 | A | 2/2000 | Moore | |
| 6,065,480 | A | 5/2000 | Mader | |
| 6,131,586 | A | 10/2000 | Flanagan | |
| 6,145,152 | A * | 11/2000 | Ward | 15/176.1 |
| 6,152,147 | A | 11/2000 | Sanchez | |
| 6,220,257 | B1 | 4/2001 | Meyer et al. | |
| 6,295,997 | B1 | 10/2001 | Dickie | |
| 6,340,027 | B1 | 1/2002 | Hagne et al. | |
| 6,484,729 | B1 * | 11/2002 | Silva | 132/200 |
| 6,601,591 | B1 * | 8/2003 | Carullo et al. | 132/320 |
| 6,895,977 | B2 | 5/2005 | Guo | |
| 7,146,989 | B2 | 12/2006 | Forssell | |
| 7,156,107 | B2 | 1/2007 | Hsu | |
| 7,305,997 | B2 | 12/2007 | Liu et al. | |
| 7,464,716 | B1 * | 12/2008 | Nygren, Jr. | 132/322 |
| 7,588,035 | B2 | 9/2009 | Ponzini | |
| 7,654,273 | B2 * | 2/2010 | Grendol et al. | 132/324 |
| 7,832,415 | B2 * | 11/2010 | Pitsis | 132/323 |
| 7,900,287 | B2 * | 3/2011 | Wildauer et al. | 4/255.11 |
| 7,987,861 | B2 | 8/2011 | Grosse | |
| 2002/0144705 | A1 | 10/2002 | Brattesani et al. | |
| 2004/0129296 | A1 * | 7/2004 | Treacy et al. | 134/6 |
| 2004/0134510 | A1 | 7/2004 | van Vilsteren et al. | |
| 2007/0240732 | A1 | 10/2007 | Landis et al. | |
| 2009/0078280 | A1 | 3/2009 | Fishman | |
| 2010/0018547 | A1 | 1/2010 | Roemuss | |
| 2010/0300481 | A1 | 12/2010 | Lavrova | |
| 2011/0155168 | A1 * | 6/2011 | Chung | 132/327 |
| 2011/0232676 | A1 | 9/2011 | Rubens et al. | |
| 2011/0265811 | A1 | 11/2011 | Lorch | |

* cited by examiner

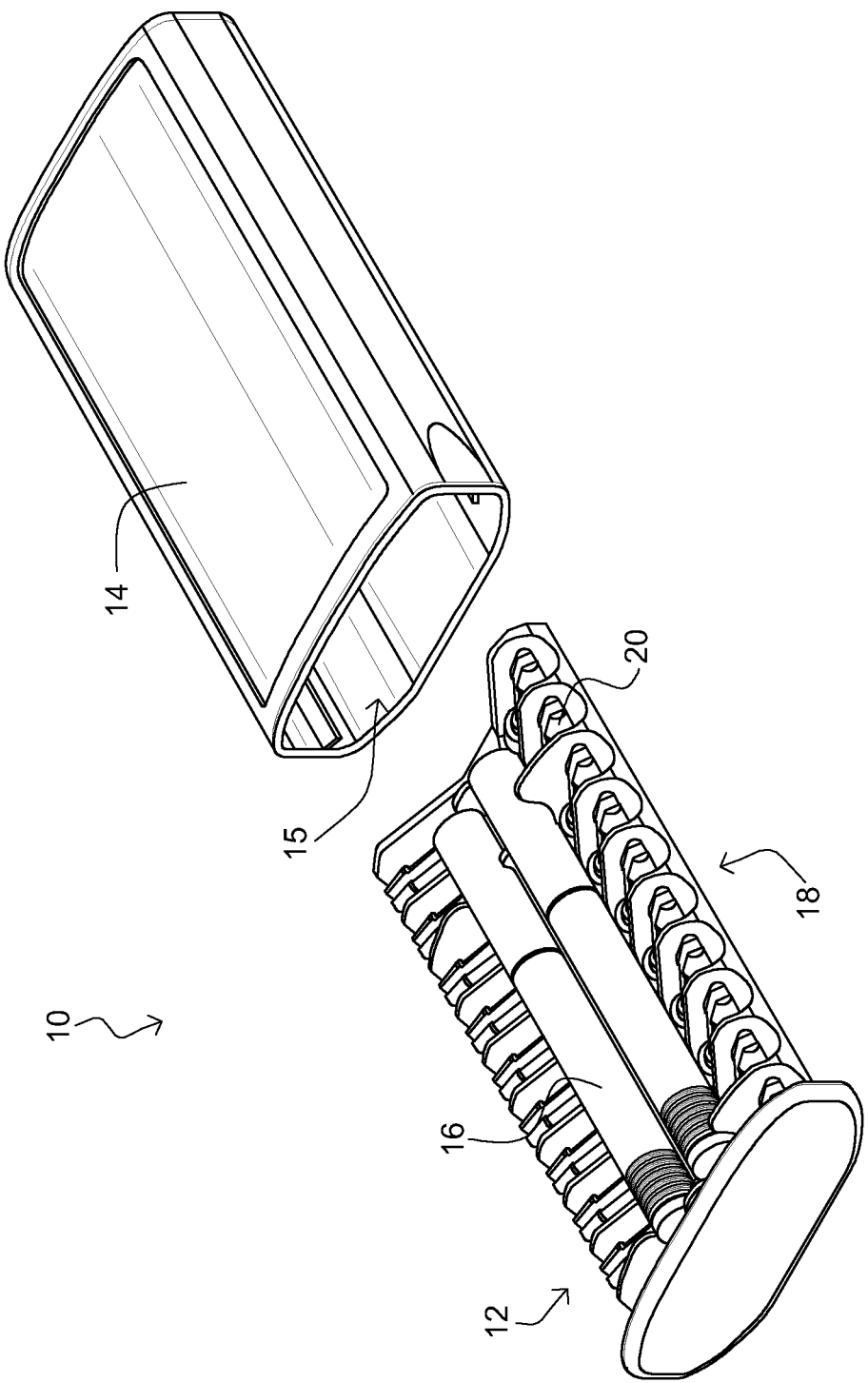

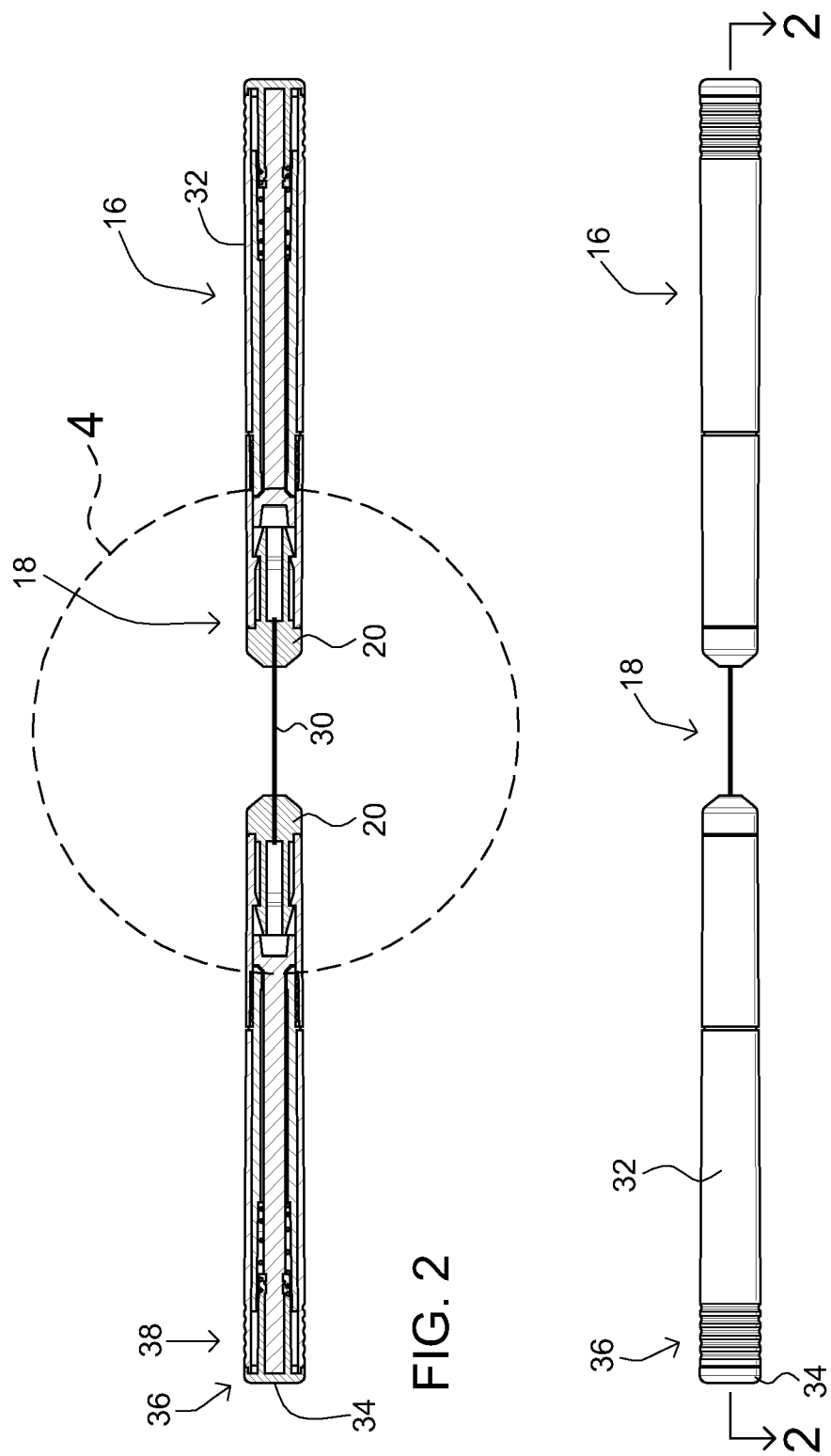

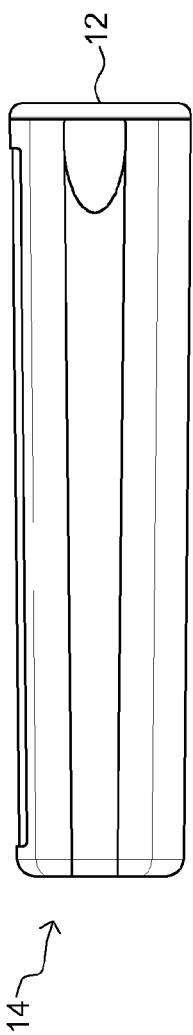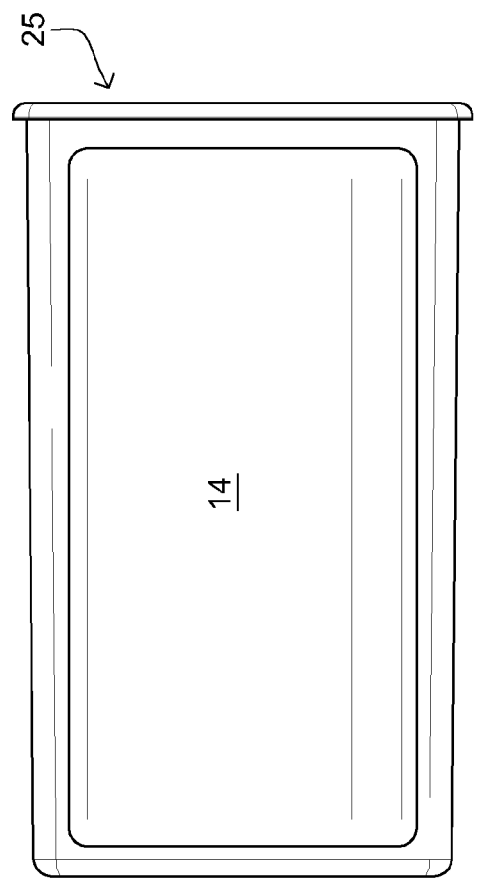

FLOSSING SYSTEM

CROSS-REFERENCE TO RELATED APPLICATIONS

This invention claims priority, under 35 U.S.C. §120, to the U.S. Provisional Patent Application No. 61/384,799 to Jeromi Stewart filed on Sep. 21, 2010, which is incorporated by reference herein.

BACKGROUND OF THE INVENTION

1. Field of the Invention

The present invention relates to dental hygiene devices, specifically to a dental flossing system.

2. Description of the Related Art

Dental floss is either a bundle of thin nylon filaments or a plastic (Teflon or polyethylene) ribbon used to remove food and dental plaque from teeth. The floss is gently inserted between the teeth and scraped along the teeth sides, especially close to the gums. Dental floss may be flavored or unflavored, and waxed or unwaxed. An alternative tool to achieve the same effect is the interdental brush or specialized plastic wands, or floss picks, have been produced to hold the floss. These may be attached to or separate from a floss dispenser. While not pinching the finger, using a wand may be awkward and also make it difficult to floss at all the angles possible with a finger. At the same time, the enhanced reach can make flossing the back teeth easier. Some improvements have been made in the field. Examples of references related to the present invention are described below in their own words, and the supporting teachings of each reference are incorporated by reference herein:

U.S. Pat. No. 6,895,977, issued to Guo, discloses a dental flossing tool for dispensing floss for cleaning the user's teeth. A handle body surrounds a cavity and has a lead riser from which dental floss is dispensed for use. The floss is wound upon a spool that rotates inside the cavity. Floss is paid out from the spool and emerges from a hole in the tip of the lead riser. A button or handle is slidably mounted upon the apparatus for controlling the longitudinal movement of a retainer within the cavity of the apparatus. By sliding the button handle forward and backward, the user can disengage and engage the retainer with a baffle attached to the spool inside the body of the apparatus. When the retainer is in contact with the baffle, the spool is prevented from rotating, thereby stopping any further floss from being dispensed. When the retainer is disengaged out of contact with the baffle, the spool is free to rotate to pay out floss. A removable protector is provided for covering the lead riser and a floss cutter blade attached to the exterior of the apparatus. The protector can be removed to the back end of the apparatus to extend its graspable portion for easier handling.

U.S. Pat. No. 6,019,109, issued to Moore, discloses a dental flossing tool and method for flossing of the teeth using that tool is provided. The tool includes two elongated, rod-shaped handle elements and a length of dental floss that is removably secured at its opposite ends to respective ones of the handle elements at their terminal ends. Each handle element is provided with a bulb at the terminal end to which the floss is attached with the bulbs being larger in transverse cross-section relative to the longitudinal axis of its handle element than is the adjacent portion of the handle element. This results in a depressed annular region in which floss is wound and functions to retain the floss on a handle element. Each handle element includes a hand-grip section disposed in remote relationship to the terminal end provided with a bulb enabling a user to grip the element in a respective hand for support thereof and independent manipulation in effecting a flossing operation. The user holds the handle elements in separated relationship to maintain the floss extending between the terminal ends taut as an operative flossing section while inserting it between a pair of adjacent teeth and moving it to effect removal of debris. At intermittent intervals the user revolves the handle elements to concurrently unreel a length of floss from one and reel a length onto the other thereby placing an unused section of floss in an operative position and placing the previously used section on a handle element for storage until being discarded upon termination of a flossing operation.

U.S. Pat. No. 5,564,446, issued to Wiltshire, discloses a dental floss device and applicator assembly comprising a pair of separate, substantially elongate members with each member having spaced apart top and bottom end portions with a gripping section located between the top and bottom end portions, a plurality of dental floss segments, and a slot formed in the top end portion of each member that has a prong protruding from the slot for releasably holding one of the dental floss segments (STRAND) within the slot. An alignment channel or groove can also be formed in the top end portion and located adjacent to the slot to hold and guide the STRAND within the alignment channel or groove without requiring a user to manipulate the STRAND with the user's fingers as the prong engages and holds the STRAND under the prong. The members are of sufficient length to allow a user to insert the members into a person's mouth with the STRAND attached to the top end portion of the members to clean all surfaces of the person's teeth without requiring the user to insert the user's fingers into the person's mouth. Further, the user does not have to manipulate the STRAND with the user's fingers when cleaning the person's teeth. The dental floss device and applicator assembly can also include a kit for storing the members and a container of dental floss segments.

U.S. Pat. No. 4,655,233, issued to Laughlin, discloses a tool for the dental flossing of teeth and a precut length of dental floss having gripping attachments secured to the ends of the length of floss. The precut length(s) of floss are configured so as to facilitate the gripping of the attachments by the flossing tool. The tool is fully operable by the use of one hand.

The inventions heretofore known suffer from a number of disadvantages which include being difficult to use, being difficult to control, being too slow, being non-durable, being dangerous to use, being unable to reach certain areas of the mouth, being non-portable, being uncomfortable to use, being expensive, being bulky, being inefficient, being limited in application, being limited in use, being limited in movement, not being ergonomic, being difficult for children to use, taking too long to use, blocking fingertip circulation, being difficult to travel with, being fragile, and being cumbersome to use.

What is needed is a flossing system that solves one or more of the problems described herein and/or one or more problems that may come to the attention of one skilled in the art upon becoming familiar with this specification.

SUMMARY OF THE INVENTION

The present invention has been developed in response to the present state of the art, and in particular, in response to the problems and needs in the art that have not yet been fully solved by currently available dental flossing devices. Accordingly, the present invention has been developed to provide an efficient and effective device for flossing teeth.

According to one embodiment of the invention, there is a flossing system that may include a cradle. The floss system may include a housing that may be configured to receive the cradle and cover a top portion thereof. The flossing system may include an array of floss cartridges that may be disposed on the cradle. The array of floss cartridges may be disposed along each side of the cradle. The array of floss cartridges may include a length of floss. The array of floss cartridges may include a pair of coupling members each may be coupled to opposite ends of the length of floss. Each floss cartridge may include a coupling structure.

The flossing system may include a pair of floss handles that may be disposed on the cradle and may be selectably coupleable to the coupling members. The cradle may include a pair of channels that may be configured to receive the pair of floss handles. The pair of floss handles may include a cylindrical body. The pair of floss handles may include a release mechanism that may be disposed within the cylindrical body and may be configured to selectably disengage the floss handle from the coupling member. The release mechanism may include an actuation member that may be disposed through a back end of the cylindrical body of each of the pair of floss handles. The pair of floss handles may each include a top aperture that may be configured to receive the coupling structure of the pair of coupling members. The coupling structure of the pair of coupling members may each include an attachment member that may have an attachment end that may be configured to retractably fit inside the top aperture of each floss handle. The pair of floss handles may each include a receiving member that may be configured to securely attach to the attachment end of the attachment member. The receiving member may be coupled to the release mechanism of the floss handle that may be configured to release the attachment end from the receiving member.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order for the advantages of the invention to be readily understood, a more particular description of the invention briefly described above will be rendered by reference to specific embodiments that are illustrated in the appended drawing(s). It is noted that the drawings of the invention are not to scale. The drawings are mere schematics representations, not intended to portray specific parameters of the invention. Understanding that these drawing(s) depict only typical embodiments of the invention and are not, therefore, to be considered to be limiting its scope, the invention will be described and explained with additional specificity and detail through the use of the accompanying drawing(s), in which:

FIG. 1 is a perspective view of a cradle and a housing of a flossing system including a flossing tool, according to one embodiment of the invention;

FIG. 2 is side cross-sectional view of a pair of floss handles of a flossing system, according to one embodiment of the invention;

FIG. 3 is a side elevational view of a pair of floss handles of a flossing system, according to one embodiment of the invention;

FIG. 7 is a side elevational view of a housing of a flossing system, according to one embodiment of the invention; and FIG. 8 is a top plan view of a housing of a flossing system, according to one embodiment of the invention.

DETAILED DESCRIPTION OF THE INVENTION

Figure 4:
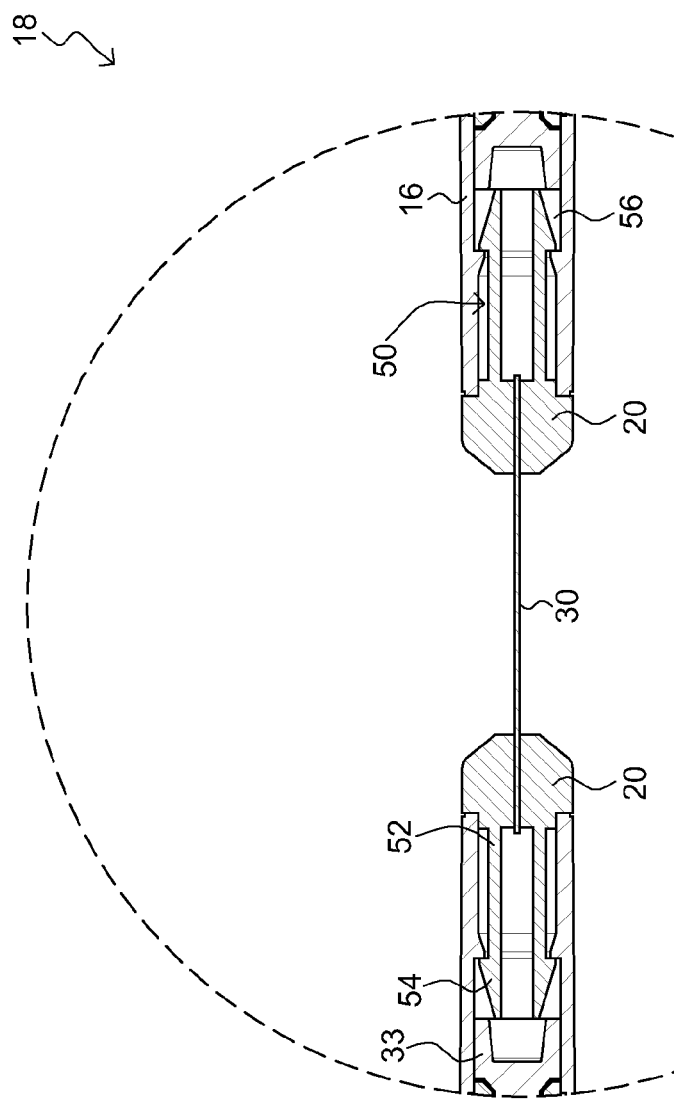
FIG. 4 is a side cross-sectional view of a floss cartridge of a flossing system, according to one embodiment of the invention.

For the purposes of promoting an understanding of the principles of the invention, reference will now be made to the exemplary embodiments illustrated in the drawing(s), and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Reference throughout this specification to an "embodiment," an "example" or similar language means that a particular feature, structure, characteristic, or combinations thereof described in connection with the embodiment is included in at least one embodiment of the present invention. Thus, appearances of the phrases an "embodiment," an "example," and similar language throughout this specification may, but do not necessarily, all refer to the same embodiment, to different embodiments, or to one or more of the figures. Additionally, reference to the wording "embodiment," "example" or the like, for two or more features, elements, etc. does not mean that the features are necessarily related, dissimilar, the same, etc.

Each statement of an embodiment, or example, is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The features, functions, and the like described herein are considered to be able to be combined in whole or in part one with another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional unrecited elements or method steps. "Comprising" is to be interpreted as including the more restrictive terms "consisting of" and "consisting essentially of."

Advantageously, the device permits users to form a C-shaped configuration during flossing, which permits enhanced removal of materials between teeth. Devices having inflexible or fixed position braces for the floss lengths do not permit this.

FIG. 1 is a perspective view of a cradle and a housing of a flossing system, according to one embodiment of the invention. There is shown a flossing system 10 including a pair of floss handles 16 and a plurality of floss cartridges 18 disposed within a cradle 12 that may be disposed within a housing 14.

The illustrated floss system 10 includes a housing 14 configured to receive the cradle 12 and cover a top portion thereof. The illustrated housing 14 includes an aperture 15 configured to be sized and shaped to receive a back profile of the cradle 12 and secure the cradle 12 therein. The housing 14 provides covering and protection to the cradle and the contents thereof from dust, fluids, disturbance and other undesired interaction during travel and other times when the system is not actively being used. A housing may include one or more flat or curved surfaces that may be coupled to one or more coupling members/devices such as but not limited to ridges, hook and loop portions, tongue and groove members, clips, hooks, and the like and combinations thereof. A housing may be fluid/water/air/etc. tight and/or may include one or more decorative elements thereon including but not limited to logos, graphics, mirrors, textured surfaces, and the like and combinations thereof.

The illustrated flossing system 10 includes a cradle 12. The illustrated cradle 12 includes a pair of channels configured to receive and support a pair of floss handles 16 thereon. The pair of channels are disposed longitudinally along a central region of the cradle 12. The pair of channels include a profile configured to be sized and shaped to receive a pair of floss handles 16. The flossing system 10 includes a pair of floss handles 16 disposed on the cradle 12. The cradle 14 also includes a plurality of dividers generating an array of receptacles for holding the floss cartridges 18. The illustrated dividers are shaped and positioned to form the pair of channels and the receptacles that nest the floss cartridges 18 and the floss handles 16. Two sets of the illustrated dividers are shaped with an extended upper region to help secure the floss handles in the channels more tightly. Channels and receptacles may be formed through a variety of structures, including but not limited to quilted flexible materials, channeled plastic/elastic materials, arrays of coupling members/materials such as but not limited to magnets, hook and loop, straps, clips, tongue and groove, and the like and combinations thereof.

The illustrated array of floss cartridges 18 is disposed within the cradle 12 in an array along the length of the cradle 12. The coupling members 20 of the cartridges 18 are disposed on each side of the cradle 14 and the floss itself (See FIG. 2) lies between paired coupling members 20. The array of floss cartridges 18 include a coupling member 20 configured to selectably couple to a floss handle 16. The illustrated coupling members 20 are configured to be extending outwardly from a central region of the cradle 12. Advantageously, the floss cartridges 18 are available for use and coupling to the floss handles 16 when the floss handles are removed from the cradle 12. Where floss cartridges are used to a point where they should be discarded, the cartridge may be discarded and another conveniently coupled to the floss handles. Accordingly, the floss handles may be reused.

The illustrated pair of floss handles 16 are sized and shaped to nest within the cradle and include one or more coupling members/devices configured to selectably coupleable to a coupling member 20 of a floss cartridge 18. The floss handles 16 include one or more devices for selectably coupling/decoupling the floss cartridges thereto, such as but not limited to connectors (such as but not limited to hooks, snaps, friction engagement, latches, pins, and the like and combinations thereof), disconnectors (such as but not limited to movable engagement devices, levers, devices that change the effective size of an object, and the like and combinations thereof), and activation members (buttons, switches, spring operated activators, and the like and combinations thereof) and the like and combinations thereof.

The floss handles are shaped and sized to permit a user to manipulate the same with their hands such that a floss filament associated with a floss cartridge may be disposed within the mouth and placed between adjacent teeth such that material may be removed therefrom for the health of the user. Advantageously, the floss handles provide leverage and extension of the users own hands thereby effectively strengthening the user in relation to the task to be performed and facilitating the dexterous use thereof. This is particularly helpful when children are using the devices as children generally lack the strength and dexterity of adults and therefore may more easily misuse or be frustrated by flossing tools designed and optimized for adults. Further, because the floss handles do not limit arcuate positioning of the floss filament, the floss may be positioned in a C-style formation about the teeth when in use. Such a formation is known to be very effective at leaning the space between adjacent teeth.

In operation a user may take a system to a location with the members coupled together within the housing. The user may withdraw the cradle from the housing and withdraw the floss handles from the cradle. The user may engage a floss cartridge with the floss handles by selectably coupling the floss cartridge therebetween. Then the user may engage in the process of flossing. Where desired, the user may push a release button or otherwise actively disengage the floss cartridge from the floss handles and may discard the floss cartridge or return it to the cradle.

FIG. 2 is side cross-sectional view of a pair of floss handles of a flossing system, according to one embodiment of the invention. There is shown a pair of floss handles 16 coupled to a floss cartridge 18 and thereby coupled to each other through the floss filament of the floss cartridge. Accordingly, the floss handles together with the floss cartridge generate a unitary flossing tool that a user may manipulate with hands to clean spaces between teeth.

The illustrated flossing system includes a pair of floss handles 16 selectably coupleable to a floss cartridge 18. The floss cartridge 18 includes a pair of coupling members 20 coupled together by a length of floss, or floss filament, 30. The pair of coupling members 20 are each coupled to opposite ends of the length of floss 30. Such coupling may be by any of various methods including but not limited to friction fitting, welding, knotted (or otherwise oversized) floss ends, and the like and combinations thereof. Floss may extend through one or more apertures through coupling members. Each floss cartridge 18 includes a coupling structure configured to selectably couple to a floss handle 16. The illustrated coupling structure includes biased extensions, or prongs, having hook-shaped heads that engage an appropriately shaped protrusion when inserted into a cavity having such a protrusion. Advantageously, when the illustrated coupling structure engages, the coupling structure snaps into place and may naturally generate a tactile and/or audible signal that cues the user to know that the coupling structure is snugly in place and ready to use.

The illustrated pair of floss handles 16 includes a cylindrical body 32 having an inner neck portion that forms a narrowed region and an expanded region that permits engagement of the hook-shaped heads thereon. The pair of floss handles 16 include a release mechanism 36 disposed within the cylindrical body 32 and configured to selectably disengage the floss handle 16 from the coupling member 20. The illustrated release mechanism 36 includes an actuation member, or button, 34 disposed through a flexible back end portion 38 of the cylindrical body 32 of each of the pair of floss handles 16. The illustrated back end portion 38 includes an accordion-style material of flexible or partially flexible material such that its effective size may be changed under force while protecting a user from pinching or other undesired effects of having ones hands near two objects that are movable relative to each other. The button 34 is functionally coupled to a bias member (spring) that is positioned and engaged with an interior of the body of the floss handle such that the spring pushes against the button and resists the depression thereof. When the button is pressed, a cup shaped member functionally coupled to the button engages with ends of the coupling member in a manner that disengages the coupling member from the floss handles so that the coupling member may be withdrawn and decoupled from the floss handle.

FIG. 3 is a side elevational view of a pair of floss handles of a flossing system, according to one embodiment of the invention. There is shown a pair of floss handles 16 coupled together by a floss cartridge 18.

The illustrated pair of floss handles 16 are coupled together by a floss cartridge 18. The floss cartridge 18 includes a pair of coupling members attached by a length of floss and configured to selectably couple to a pair of floss handles 16. The illustrated pair of floss handles 16 each include a cylindrical body 32. The pair of floss handles 16 includes a release mechanism 36 disposed within the cylindrical body 32 and configured to selectably disengage the floss handle 16 from a coupling member of the floss cartridge 18. The release mechanism 36 includes an actuation member 34 disposed through a back end of the cylindrical body 32 of each of the pair of floss handles 16.

FIG. 4 is a side cross-sectional view of a floss cartridge of a flossing system, according to one embodiment of the invention. There is shown a floss cartridge 18 including a pair of engaged coupling members 20 and a length of floss 30.

The illustrated floss cartridge 18 includes a length of floss 30. The floss cartridge 18 includes a pair of coupling members 20 each coupled to opposite ends of the length of floss 30. Each floss cartridge 18 includes a coupling structure 50. The coupling structure 50 of the pair of coupling members 20 each includes an attachment member 52 having an attachment end 54 configured to retractably fit inside a top aperture of a floss handle 16. The pair of floss handles 16 each include a receiving member 56 configured to securely attach to the attachment end 54 of the attachment member 52. The receiving member 56 is coupled to a release mechanism of the floss handle 16 that is configured to release the attachment end 54 from the receiving member 56. The attachment end 54 is adjacent a detachment member 33 that includes a cup-shaped end configured to engage the attachment member in a manner that causes the attachment member to disengage with the floss handle when the detachment member is moved relative to the attachment end. In the illustrated example, the detachment member 33 is moved towards the attachment end thereby engaging with the ramp-shaped end of the attachment end and causing the same to be displaced towards the main axis of the floss handle. This motion disengages the hook-shaped portion of the attachment end from the interior surface of the floss handle and thereby permits the user to detach the same from the floss handle.

Figures 5, 6:
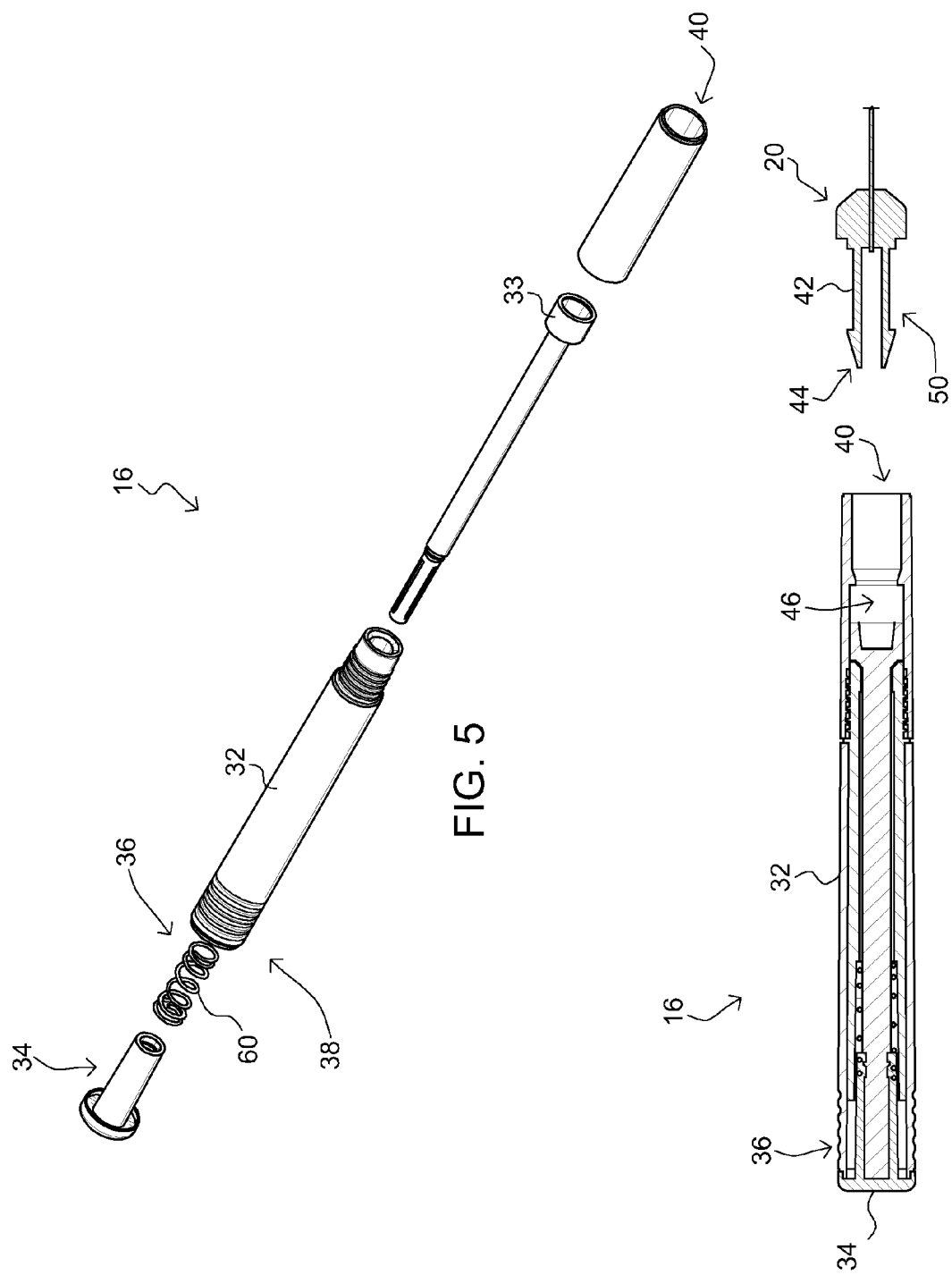
FIG. 5 is an exploded view of a floss handle of a flossing system, according to one embodiment of the invention.
FIG. 6 a side cross-sectional view of a floss handle of a flossing system, according to one embodiment of the invention.

FIG. 5 is an exploded view of a floss handle of a flossing system, according to one embodiment of the invention. There is shown a floss handle 16 including a cylindrical body 32, and a release mechanism 36.

The illustrated floss handle 16 includes a cylindrical body 32. The cylindrical body 32 is configured to support and protect the components of the floss handle. The cylindrical body 32 is configured to provide a rigid structure to manipulate and maneuver a length of floss between teeth. The floss handle 16 includes a release mechanism 36 disposed within the cylindrical body 32 and configured to selectably disengage the floss handle 16 from a coupling member of a floss cartridge. The release mechanism 36 includes a biased member 60 configured to compression release a coupling member from the floss handle 16. The release mechanism 36 includes an actuation member 34 disposed through a back end 38 of the cylindrical body 32 of the floss handle 16. The floss handle 16 includes a top aperture 40 configured to receive a coupling structure of a coupling member of a floss cartridge of a flossing system. The floss handle 16 includes a detachment member 33 that includes a cup-shaped end configured to engage an attachment member in a manner that causes the attachment member to disengage with the floss handle 16 when the detachment member 33 is moved relative to the attachment end.

FIG. 6 a side cross-sectional view of a floss handle of a flossing system, according to one embodiment of the invention. There is shown a floss handle 16 including a cylindrical body 32, a release mechanism 36, and a receiving member 46.

The illustrated floss handle 16 includes a cylindrical body 32. The floss handle 16 includes a release mechanism 36 disposed within the cylindrical body and be configured to selectably disengage the floss handle 16 from a coupling member 20 of a floss cartridge. The release mechanism 36 includes an actuation member 34 disposed through a back end of the cylindrical body 32 of the floss handle 16. The floss handle 16 includes a top aperture 40 configured to receive a coupling structure 50 of the coupling member 20. The coupling structure 50 of the coupling member 20 includes an attachment member 42 configured to couple to the floss handle 16. The attachment member 42 includes an attachment end 44 configured to retractably fit inside the top aperture 40 of the floss handle 16. The illustrated attachment member 42 includes a pair of opposing flanges configured to compress toward one another and couple to a receiving member 46 of the floss handle. The attachment end 44 includes an angled protrusion disposed on an end of a flange and configured to secure the attachment member 42 to the floss handle. The receiving member 46 is configured to securely attach to the attachment end 44 of the attachment member 42. The receiving member 46 is coupled to the release mechanism 34 of the floss handle 16 and configured to release the attachment end 44 from the receiving member 46. The receiving member 46 includes a cavity larger than the cavity of the top aperture of the floss handle, thereby securing the angled protrusions of the attachment member therein.

Looking at FIGS. 5 and 6, there is shown a floss handle 16 that is selectably coupleable to a coupling member 20, including: a gripping region formed by a cylindrical body 32, and a release mechanism 36 including a shaft (extending from detachment member 33) disposed within the cylindrical body 32, extending through an entirety of the gripping region, and configured to selectably disengage the floss handle 16 from the coupling member 20 when actuated, and an actuation member 34 functionally coupled to the shaft (extending from detachment member 33) and disposed at an end of each floss handle that is distal-most with respect to the associated coupling member 20 when coupled thereto FIGS. 7 and 8 illustrate a side elevational view and a top plan view of a housing of a flossing system, according to one embodiment of the invention. There is shown a housing 14 of a flossing system.

The illustrated housing 14 is shaped to secure and support a cradle 12 of a flossing system. The cradle 12 is configured to be disposed within the housing 14. The illustrated cradle 12 includes an aperture cover coupled to an end of the cradle 12. The aperture cover 25 is configured to cover an aperture of the housing 14. The illustrated aperture cover 25 is configured to seal the cradle 12 within the housing 14 and secure the cradle therein. The illustrated housing 14 is sized and shaped to receive the cradle 12 and secure the cradle 12 therein. Advantageously, the housing and cover facilitate convenient storage and travel in a manner that protects the contents and reduces the effective size of the system/kit to a minimal level.

In operation of one embodiment of the invention, a user picks up a floss handle with one hand and another floss handle with the other hand. The user couples a coupling member through a top aperture of each floss handle, thereby coupling a floss cartridge to the pair of floss handles. The coupled device resembles a miniature nunchaku, a traditional Japanese weapon that has gained popularity as a form to be emulated in some modern toys and game devices. This resemblance of the tools to a toy is advantageous in the pursuit of teaching children to floss because it associates the tools with fun. The user manipulates and maneuvers the pair of floss handles to floss between the teeth of the user. The user, upon finishing flossing the user's teeth, actuates an actuation member of a release mechanism of each floss handle. The user presses down on a back end of the floss handle and disengages the pair of coupling members from the pair of floss handles. The portions of the device may then be stored for future use.

The following are "statements" or, in other words, non-limiting examples of various embodiments of the invention:

1. A flossing system or tool, comprising
   a) a cradle;
   b) a floss cartridge, including:
     b1) a length of floss; and
     b2) a pair of coupling members each coupled to opposite ends of the length of floss; wherein each is provided with a coupling structure; and
   c) a pair of floss handles disposed on the cradle and selectably coupleable to the coupling members, including;
     c1) a cylindrical body, and
     c2) a release mechanism disposed within the cylindrical body and configured to selectably disengage the floss handle from the coupling member.
2. The flossing system or tool of statement 1 further comprising a housing configured to receive the cradle and cover a top portion thereof, wherein the floss cartridge is one of an array of floss cartridges according to statement 1 which are disposed on the cradle.
3. The system or tool of statement 2, wherein the array of floss cartridges are disposed along each side of the cradle.
4. The system or tool of any preceding statement, wherein the cradle is provided with a pair of channels configured to receive the pair of floss handles.
5. The system or tool of any preceding statement, wherein the release mechanism is provided with an actuation member disposed through a back end of the cylindrical body of each of the pair of floss handles.
6. The system or tool of any preceding statement, wherein the pair of floss handles is each provided with a top aperture configured to receive the coupling structure of the pair of coupling members.
7. The system or tool of any preceding statement, wherein the coupling structure of the pair of coupling members is each provided with an attachment member having an attachment end configured to retractably fit inside the top aperture of each floss handle.
8. The system or tool of any preceding statement, wherein the pair of floss handles each includes a receiving member configured to securely attach to the attachment end of the attachment member.
9. The system or tool of any preceding statement, wherein the receiving member is coupled to the release mechanism of the floss handle configured to release the attachment end from the receiving member.
10. The flossing system or tool of any preceding statement wherein the release mechanism includes an actuation member disposed through a back end of the cylindrical body of each of the pair of floss handles; wherein the pair of floss handles is each provided with a top aperture configured to receive the coupling structure of the pair of coupling members; wherein the coupling structure of the pair of coupling members each include an attachment member having an attachment end configured to retractably fit inside the top aperture of each floss handle; wherein the pair of floss handles each include a receiving member configured to securely attach to the attachment end of the attachment member; wherein the receiving member is coupled to the release mechanism of the floss handle configured to release the attachment end from the receiving member.

In one non-limiting embodiment, there may be a compact and convenient travel kit including a pair of cradles each holding ten floss cartridges having floss lengths of approximately three-quarters of an inch, a pair of floss handles, a durable and stylish housing and a collectible character trading card.

It is understood that the above-described embodiments are only illustrative of the application of the principles of the present invention. The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

For example, although the figures illustrate a particular configuration and set of components for the coupling structures, it is understood that other structures will fall within the scope of the claims.

Additionally, although the figures illustrate particular sizes, shapes and size relationships of various portions and/or members, it is understood that the sizes, shapes and relational sizes of various embodiments of the present invention are plethoric.

It is also envisioned that a plurality of types of floss may be utilized in various embodiments of the present invention, including but not limited to cylindrical floss, tape-style floss, multi-filament floss, waxed/unwaxed floss, flavored floss, colored floss, stylized floss, and decorated floss and the like and combinations thereof.

It is expected that there could be numerous variations of the design of this invention. An example is that the floss handles may be decorated to resemble licensed characters, specific weapons, construction tool handles, and the like and combinations thereof.

Finally, it is envisioned that the components of the device may be constructed of a variety of materials, including but not limited to metals, ceramics, plastics, resins, fibers, minerals, polymers, composites, and the like and combinations thereof.

Thus, while the present invention has been fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims. Further, it is contemplated that an embodiment may be limited to consist of or to consist essentially of one or more of the features, functions, structures, methods described herein.

What is claimed is:

1. A flossing system comprising:
   a) a cradle;
   b) an array of floss cartridges disposed on the cradle; wherein the array of floss cartridges are disposed along each side of the cradle and including: a length of floss, and a pair of coupling members each coupled to opposite ends of the length of floss;
   c) a pair of floss handles disposed on the cradle and selectably coupleable to the coupling members, including: a gripping region formed by a cylindrical body, extending through an entirety of the gripping region, and configured to selectably disengage the floss handle from the coupling member when actuated, and wherein the release mechanism includes an actuation member functionally coupled to the shaft and extending backwardly from a back end of the cylindrical body of each floss handle that is distal-most with respect to the associated coupling member when coupled thereto such that a user may grasp the floss handles together and strike the back end of each of the floss handles against a surface, thereby depressing the actuation member and thus ejecting the attached floss cartridge from the floss handles; wherein the pair of floss handles each include a top aperture configured to receive a coupling structure of the pair of coupling members; wherein the coupling structure of the pair of coupling members each include an attachment member having an attachment end configured to retractably fit inside the top aperture of each floss handle; wherein the pair of floss handles each include a receiving member configured to securely attach to the attachment end of the attachment member; wherein the receiving member is coupled to the release mechanism of the floss handle configured to release the attachment end from the receiving member; wherein the gripping region does not include the actuation member; wherein the attachment end includes a first angled protrusion disposed on an end of a first flange and is configured to secure the coupling member to the floss handle; and wherein the shaft of the release mechanism includes a cup-shaped end configured to engage the angled protrusion of the attachment end in a manner that causes the coupling member to disengage from the floss handle when the cup-shaped end is moved relative to the attachment end; and
   d) a housing configured to receive the cradle and cover a top portion thereof.

2. The flossing system of claim 1, wherein at the back end of the cylindrical body, the release mechanism includes a flexible accordion-style portion such that its effective size may be changed under force while protecting a user from pinching.

3. The flossing system of claim 1, wherein the attachment end includes a second angled protrusion disposed on an end of a second flange opposing the first flange such that the opposing first and second flanges are configured to move toward one another.

4. The flossing system of claim 2, wherein the attachment end includes a second angled protrusion disposed on an end of a second flange opposing the first flange such that the opposing first and second flanges are configured to move toward one another.

* * * * *